(12) United States Patent
Vahlensieck et al.

(10) Patent No.: US 11,612,760 B2
(45) Date of Patent: Mar. 28, 2023

(54) COSMETIC METHOD AND APPARATUS FOR THE TREATMENT OF SKIN TISSUE USING TWO WAVELENGTHS OF LASER ENERGY

(71) Applicant: LUMENIS LTD., Yokneam (IL)

(72) Inventors: Jay M. Vahlensieck, Livermore, CA (US); Patrick Reichert, Dublin, CA (US); David Youngquist, San Jose, CA (US); Christopher Michael Bradley, Orinda, CA (US); Jeffrey A. Tilley, La Honda, CA (US); Alan Scott Crarer, Santa Cruz, CA (US)

(73) Assignee: LUMENIS BE LTD., Yokneam (IL)

( * ) Notice: Subject to any disclaimer, the term of this patent is extended or adjusted under 35 U.S.C. 154(b) by 116 days.

(21) Appl. No.: 17/113,000

(22) PCT Filed: Jun. 13, 2019

(86) PCT No.: PCT/US2019/036890
§ 371 (c)(1),
(2) Date: Dec. 5, 2020

(87) PCT Pub. No.: WO2019/241465
PCT Pub. Date: Dec. 19, 2019

(65) Prior Publication Data
US 2021/0316155 A1    Oct. 14, 2021

Related U.S. Application Data

(60) Provisional application No. 62/684,875, filed on Jun. 14, 2018.

(51) Int. Cl.
*A61N 5/06*   (2006.01)
*A61N 5/067*  (2006.01)
*G02B 26/10*  (2006.01)

(52) U.S. Cl.
CPC ........... *A61N 5/0616* (2013.01); *A61N 5/067* (2021.08); *G02B 26/105* (2013.01); *A61N 2005/0644* (2013.01); *A61N 2005/0659* (2013.01)

(58) Field of Classification Search
CPC .... G02B 26/105; A61N 5/0616; A61N 5/067; A61N 2005/0644
See application file for complete search history.

(56) References Cited

U.S. PATENT DOCUMENTS

RE38,670 E    12/2004  Asah et al.
2003/0220633 A1   11/2003  Angeley et al.
(Continued)

OTHER PUBLICATIONS

Search Report—Corresponding European Application No. 19820235, dated Feb. 23, 2022, 8 pages.
(Continued)

*Primary Examiner* — Lynsey C Eiseman
*Assistant Examiner* — Jessica L Mullins
(74) *Attorney, Agent, or Firm* — ISUS Intellectual Property PLLC; Anthony Jason Mirabito (57) ABSTRACT

A method of treatment of skin tissue with two laser devices of unequal wavelengths comprising the steps of: (1) activating the two laser devices simultaneously to produce two laser beams of unequal wavelength; (2) directing the two laser beams into a handpiece having a distal tip to direct the laser beams onto the skin tissue; (3) directing the two laser beams within the handpiece to an adjustable beam deflector; and, (4) the adjustable beam deflector directing the two laser beams onto the skin tissue to produce a pattern of laser spots simultaneously but separated from one another.

14 Claims, 9 Drawing Sheets

(56) References Cited

U.S. PATENT DOCUMENTS

| | | | |
|---|---|---|---|
| 2006/0217695 A1 | 9/2006 | Debenedictis et al. | |
| 2007/0167936 A1* | 7/2007 | Samain | A45D 19/00 606/9 |
| 2008/0154248 A1 | 6/2008 | Dunki-Jacobs | |
| 2008/0287930 A1* | 11/2008 | Rapoport | B23K 26/0096 606/9 |
| 2009/0118720 A1 | 5/2009 | Black et al. | |
| 2012/0253331 A1 | 10/2012 | Liu et al. | |
| 2012/0283803 A1 | 11/2012 | Liu et al. | |
| 2013/0197480 A1* | 8/2013 | McDaniel | A61M 37/00 604/522 |
| 2014/0107635 A1 | 4/2014 | Poran et al. | |

OTHER PUBLICATIONS

Search Report and Written Opinion—Corresponding PCT Application No. PCT/US2019/036890, dated Aug. 29, 2019, 8 pages.

* cited by examiner

COSMETIC METHOD AND APPARATUS FOR THE TREATMENT OF SKIN TISSUE USING TWO WAVELENGTHS OF LASER ENERGY

RELATED APPLICATIONS

This application is a continuation application of PCT Application No. PCT/US2019/36890, filed Jun. 13, 2019, which relates to and claims priority to U.S. provisional application Ser. No. 62/684,875, filed Jun. 14, 2018.

FIELD OF THE INVENTION

The present invention relates to cosmetic method and apparatus for the treatment of skin tissue. In particular, the present invention relates to cosmetic method and apparatus of the treatment of skin tissue using two wavelengths of laser energy.

BACKGROUND

This application relates to a cosmetic apparatus for treating skin conditions using two different wavelengths of laser energy, applied to the skin simultaneously but spatially separated relative to each other.

BACKGROUND OF THE PRESENT INVENTION

The use of laser light to treat skin conditions is a common practice in aesthetic procedures and well documented in the literature. Some procedures deposit multiple laser wavelengths to the skin tissue. This is normally accomplished by exposing the tissue to single wavelength handpieces in successive phases of treatments. It is to the improvement of apparatus and methods of more effectively treating skin tissue while reducing the time duration of the treatment, and without causing excess pain to the patient that the present invention is directed.

SUMMARY OF THE PRESENT INVENTION

In an aspect, a laser treatment device for treating skin tissue includes: at least two laser energy generating engines, wherein each of the at least two laser generating engines operating to produce laser beams at different wavelengths; it also may include a handpiece for receiving the at least two laser beams generated by the at least two laser energy generating engines, the handpiece being in operative connection with the at least two laser energy generating engines; the handpiece may include a proximal end and a distal tip, further comprising one or more mirrors along a light path to receive each of the at least two laser beams from the proximal end and to convey the at least two laser beams to the tip of the handpiece; an adjustable beam deflector is positioned along the light path between the distal and the proximal end of the handpiece; further, a controller is included in the laser treatment device to control the activation of the at least two laser energy generating engines and control movement of the adjustable beam deflector. The controller may be being configured to: (1) cause activation of both of the at least two laser energy generating engines at the same time and (2) cause the movement of the adjustable beam deflector such that the at least two laser beams are deflected to pass through the distal tip of the handpiece and impinge as laser spots onto the skin tissue at the same time but separated by a distance and non-overlapping.

In another aspect, the at least two laser generating engines produce laser beams of 1410 nm and 1927 nm, and the adjustable beam deflector is one of: a galvo mirror or a MEMs device. The beam adjustable beam deflector is positioned proximal of the handpiece tip.

In a further aspect, the one or more mirrors are positioned proximal of the adjustable beam deflector and bend the at least two laser beams at an angle with respect to the handpiece. The device may further comprise one or more lenses distal of the adjustable beam deflector to focus the at least two laser beams.

In yet another aspect, the device further comprises a plurality of rollers mounted distally of the tip, the rollers having an axis of rotation perpendicular with respect to the optical path, such that rollers may be translated along the skin tissue. The at least one of the plurality of rollers may include an encoding device, and wherein rotation of the plurality of rollers is configured to cause the controller to activate the at least two laser energy generating engines.

In an aspect, the handpiece further includes one or more passageways along the light path from the proximal end to the distal end of the handpiece to carry air from an external source to the distal end of the handpiece and then the skin tissue. The external source provides cooling air to cool the skin tissue and to impinge upon and cool the plurality of rollers.

In an aspect, a method for treating skin tissue includes: providing at least two laser energy generating engines, wherein each of the at least two laser generating engines operate to produce laser beams at different wavelengths; providing a handpiece for receiving the at least two laser beams generated by the at least two laser energy generating engines, the handpiece being in operative connection with the at least two laser energy generating engines; wherein the handpiece includes a proximal end and a distal tip, further comprising one or more mirrors along a light path to receive each of the at least two laser beams from the proximal end and to convey the at least two laser beams to the tip of the handpiece; providing an adjustable beam deflector along the light path between the distal and the proximal end of the handpiece; providing a controller in the laser treatment device to control the activation of the at least two laser energy generating engines and control movement of the adjustable beam deflector. The method includes: the controller: (1) causing activation of both of the at least two laser energy generating engines at the same time and (2) causing movement of the adjustable beam deflector such that the at least two laser beams are deflected to pass through the distal tip of the handpiece and impinge as laser spots onto the skin tissue at the same time but separated by a distance and non-overlapping. The at least two laser generating engines produce laser beams of 1410 nm and 1927 nm and the adjustable beam deflector is one of: a galvo mirror or a MEMs device. The adjustable beam deflector is positioned proximal of the handpiece tip.

In another aspect, the one or more mirrors are positioned proximal of the adjustable beam deflector and bend the at least two laser beams at an angle with respect to the handpiece, and one or more lenses are provided distally of the adjustable beam deflector to focus the at least two laser beams. A plurality of rollers may be mounted distally of the tip, the rollers having an axis of rotation perpendicular with respect to the optical path, such that rollers may be translated along the skin tissue. At least one of the plurality of rollers includes an encoding device, and wherein rotation of the plurality of rollers causing the controller to activate the at least two laser energy generating engines.

In a further aspect, the handpiece further includes one or more passageways along the light path from the proximal end to the distal end of the handpiece to carry air from an external source to the distal end of the handpiece and then the skin tissue. The external source provides cooling air to cool the skin tissue and to impinge upon and cool the plurality of rollers.

In an aspect, a method of treatment of skin tissue with two laser devices of unequal wavelengths includes the steps of: (1) activating the two laser devices simultaneously to produce two laser beams of unequal wavelength; (2) directing the two laser beams into a handpiece having a distal tip to direct the laser beams onto the skin tissue; (3) directing the two laser beams within the handpiece to an adjustable beam deflector; and, (4) the adjustable beam deflector directing the two laser beams onto the skin tissue to produce a pattern of laser spots simultaneously but separated from one another.

DETAILED DESCRIPTION OF THE PRESENT INVENTION

I. The Basic Device Structure

According to one aspect, the present invention discloses a dual wavelength non-ablative fractional laser device for resurfacing and for dyspigmentation treatments. The treatments are preferably performed in three distinct treatment modes: laser wavelength 1 only, laser wavelength 2 only and laser wavelengths 1 and 2 simultaneously. The lasers may be fired with powers of ~5 W and ~3 W for skin resurfacing and pigment treatments respectively. Both lasers are fired through a single, compact handpiece that includes a means of coupling the energy from the lasers to the handpiece, a folded optical system to facilitate a compact and ergonomically friendly design, structure for propagating the laser energy of both beams along a quasi-common beamline and a mechanism, such as a galvo scanning mirror system or a MEMs device to direct the light beams to targeted areas of the skin tissue.

The handpiece may have three main functions or attributes: (1) it houses the optical delivery system (to be detailed herein); (2) it contains the galvo system which allows for the scanning of repeated lines of spots impinging on the target tissue, those being traversed to the direct movement on the skin, creating a raster-like pattern of spots, as illustrated by way of example only in FIGS. 1 and 2, to be discussed in detail herein; (3) it mounts a delivery tip which serves a target skin tissue contact surface as well as may provide a handpiece velocity measurement relative to movement across the skin; the laser treatment rate may be adjusted according to the velocity as well as desired targeted spot density on the skin tissue, as discussed further herein; the delivery tip may also contain elements which serve to cool the skin tissue.

Figure 2:
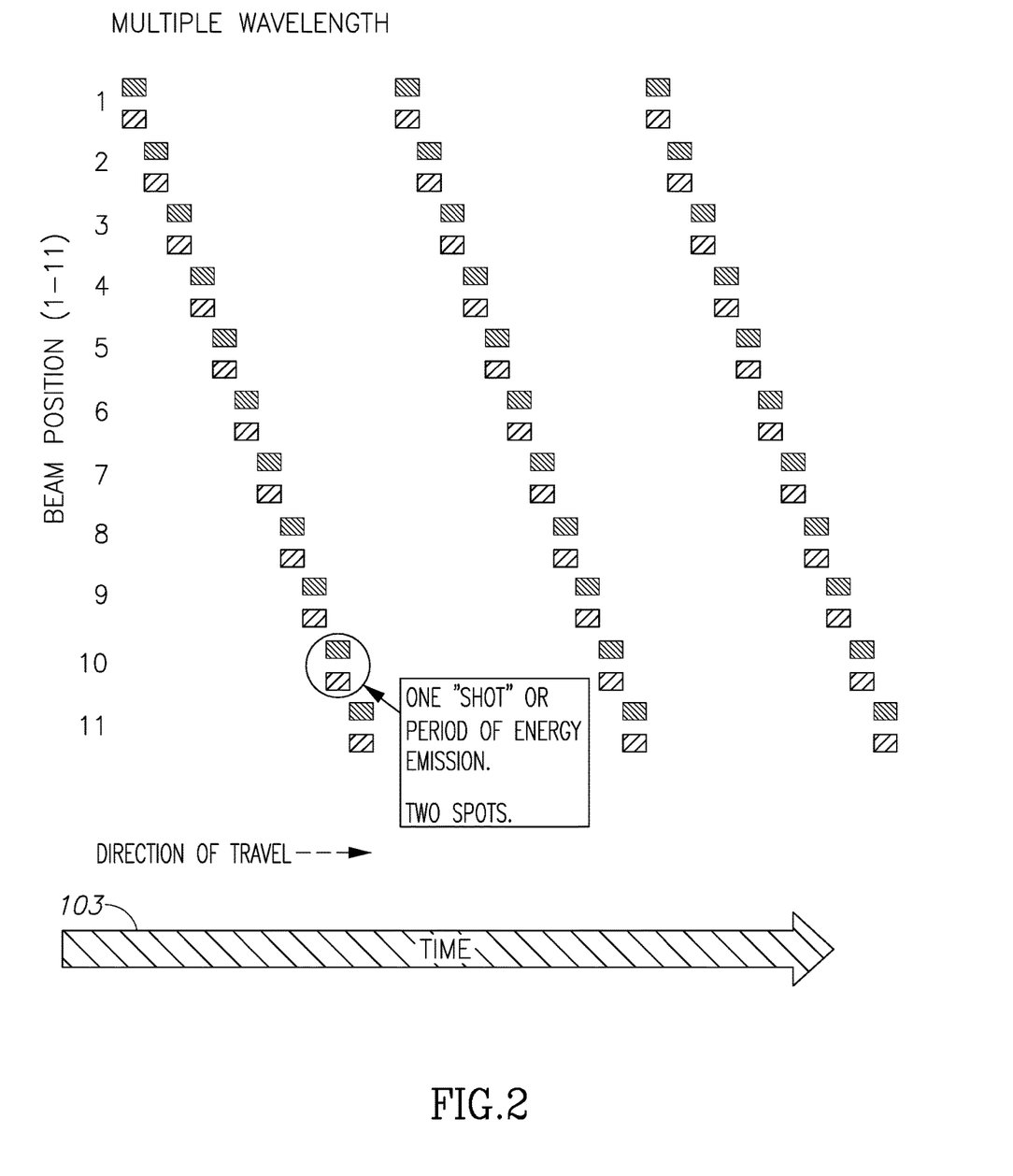
Figure 2A:
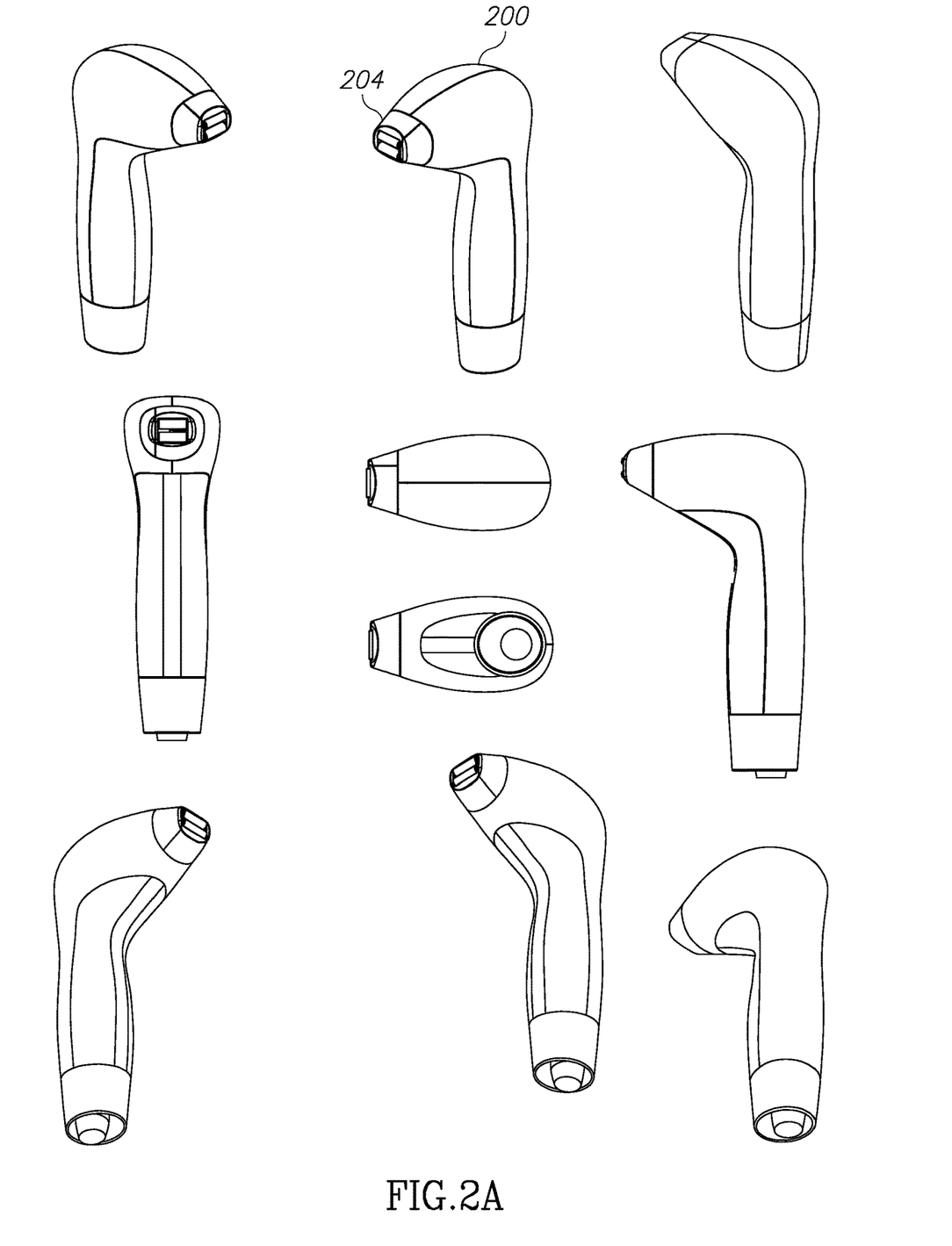
FIGS. 2A and 2B illustrate the shape and design aspects of the handpiece and associated console of the present invention.

One embodiment of the handpiece 200 is illustrated in FIG. 2A, which illustrates further views of the handpiece from a few different perspectives and orientations and which show the overall shape and other design attributes of the handpiece.

Figure 2B:
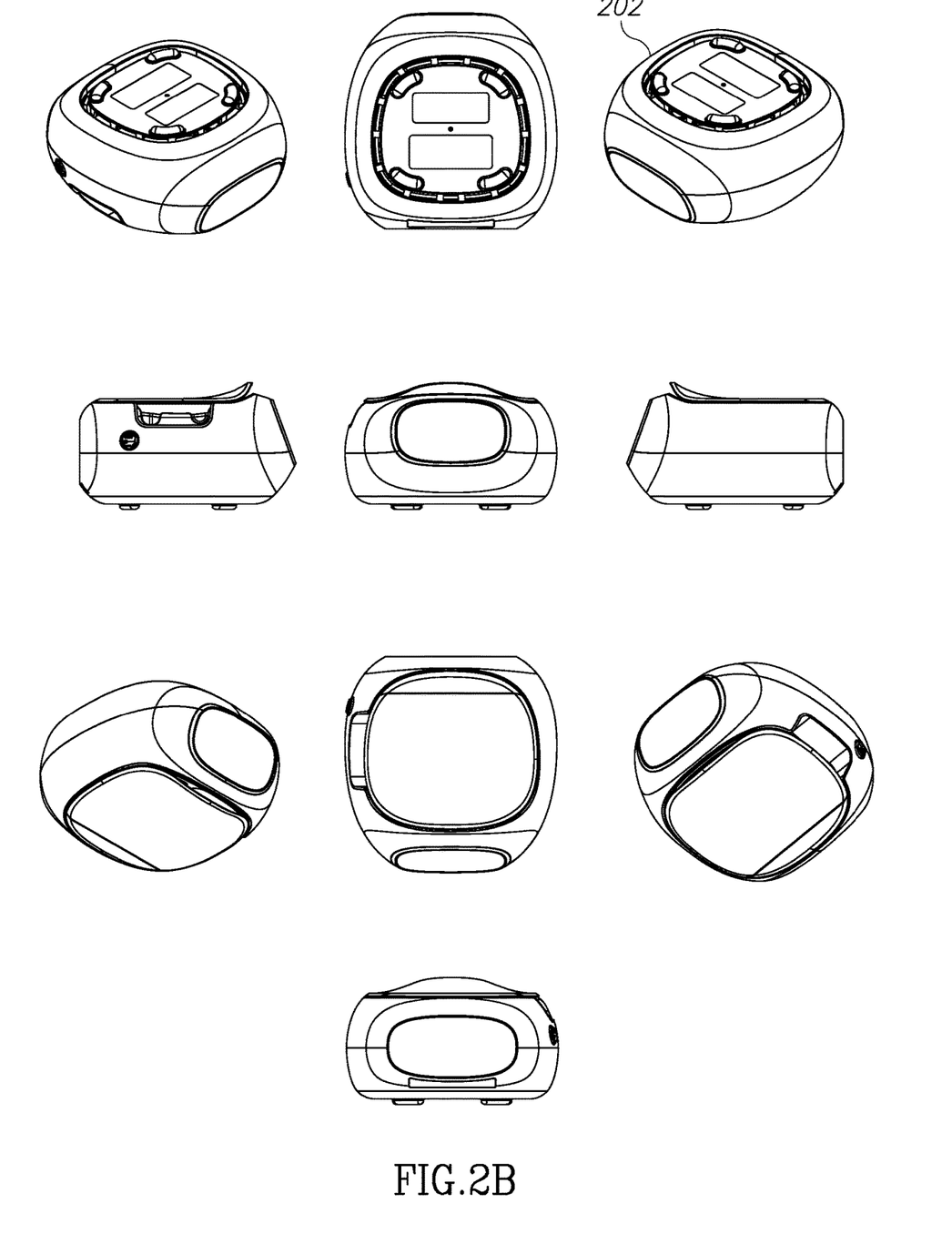

FIG. 2B illustrates an embodiment of a console 202 which may be used in junction with the handpiece of FIG. 2A and is shown from a number of different perspectives and orientations. The console may contain, as will be detailed herein, among other things, one or more laser beam sources, a programmable controller, suitable computer system and memory, a GUI, control buttons, and a source of cooling air to be provided to the handpiece.

The two wavelengths selected may be those generally accepted in the industry for use in skin rejuvenation and dyspigmentation treatments, that is, wavelengths in the range of 14XX nm to 19XX nm. The embodiment of the device described herein may employ 1410 nm and 1927 nm wavelengths, although other suitable lasers with different wavelengths may be implemented.

The present invention is directed to fractional skin rejuvenation of the non-ablative type. Non-ablative skin rejuvenation employs a laser or lasers to improve the appearance of wrinkles, brown spots and minor scars by creating heat in the skin tissue without injuring the skin tissue surface. The heat generated by the laser promotes collagen production which causes the skin tissue to tighten and appear young and healthy. Non-ablative laser actions are often fractionated so that they deliver heat into the skin tissue in many tiny, deep columns known in the industry as microthermal zones with intervening tissue areas that are not treated with the laser or lasers. It has been found that this type of treatment allows the skin tissue to heal faster than if the entire area is treated, and, further, this approach lessens the recovery period and reduces the number of possible complications.

In the present invention, both laser wavelengths, 1410 nm and 1927 nm, are non-ablative laser sources. Two different wavelengths are employed in the present invention to treat two different skin tissue layers.

The 1410 nm laser is suitable for deep tissue treatment and is indicated for dermatological procedures requiring the coagulation of soft tissue. Such treatments include, for example, treatment of periorbital wrinkles, acne scars, and surgical scars. In addition, treatments include photocoagulation of pigmented lesions such as but not limited to age spots, sunspots, and dyschromia, as well as skin resurfacing procedures.

The 1927 nm laser, by contrast, is for more shallower surface related treatments. This wavelength is indicated for dermatological procedures requiring the coagulation of soft tissue in the treatment of actinic keratosis, photocoagulation of pigmented lesions, such as, but not limited to age spots, sunspots and freckles.

The distal end (204 in FIG. 2A) of the handpiece may be placed in contact with the skin tissue and "rolled" over it. A suitable optical tracking system (as described in connection with FIG. 5 herein) may be incorporated into the handpiece to track, by way of example only, the extent of treatment performed. An optical or other sensing systems may be utilized to determine the extent of treatment provided to the skin tissue. In addition to the sensors described in detail below, other known motion sensors for use in light-based devices are shown in U.S. Pat. Nos. 6,171,302 and 6,758,845, both of which are assigned to the assignee of the present invention(s) and application.

In addition, a magnetic tracking device (as described in connection with FIG. 5 herein) may be utilized that uses a magnetic sensor that is paired in a known manner with one or more of the two rollers discussed below.

II. Detailed Optical System

Figure 3:
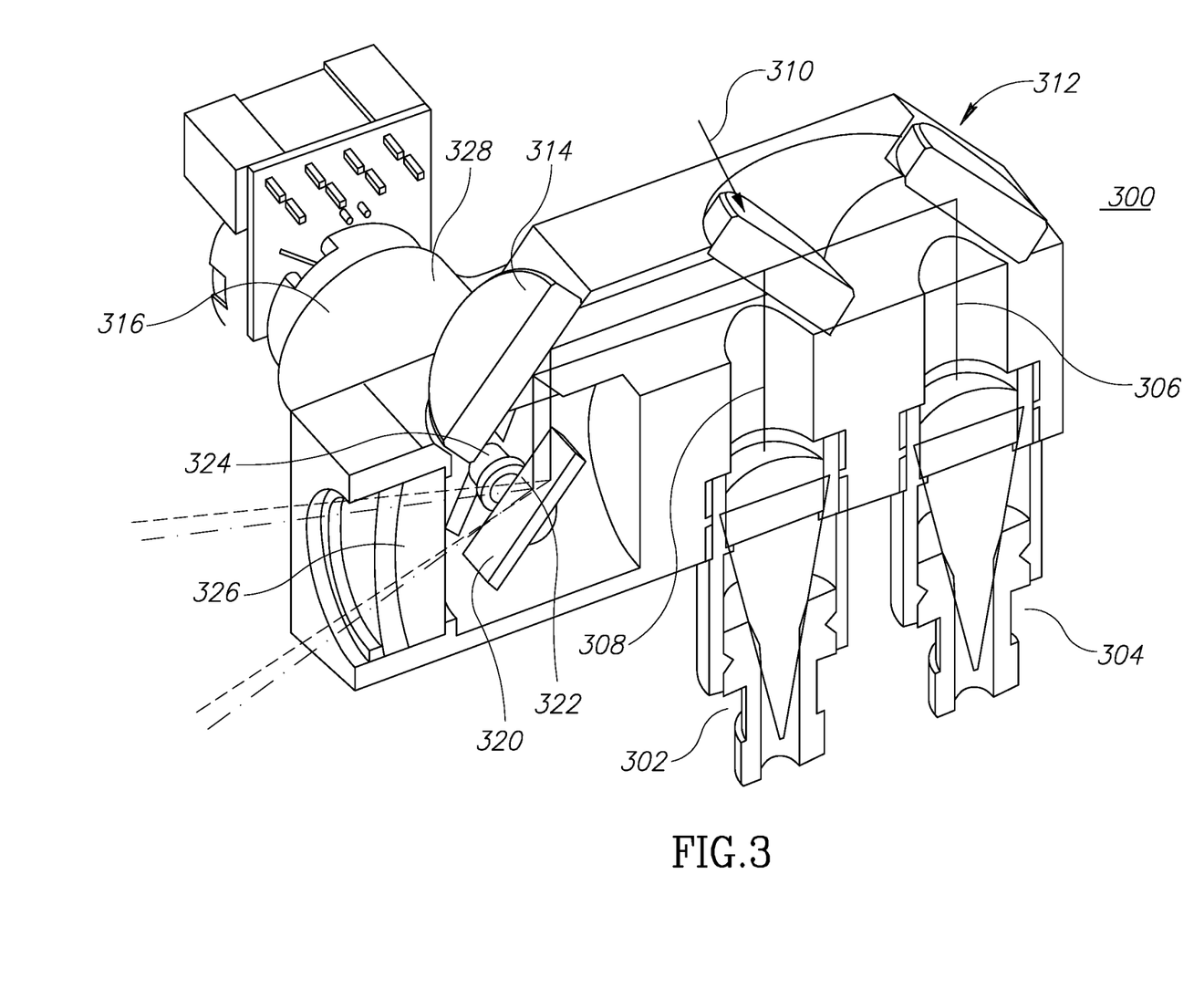
FIG. 3 illustrates the optical system setup of the present invention.
Figure 4:
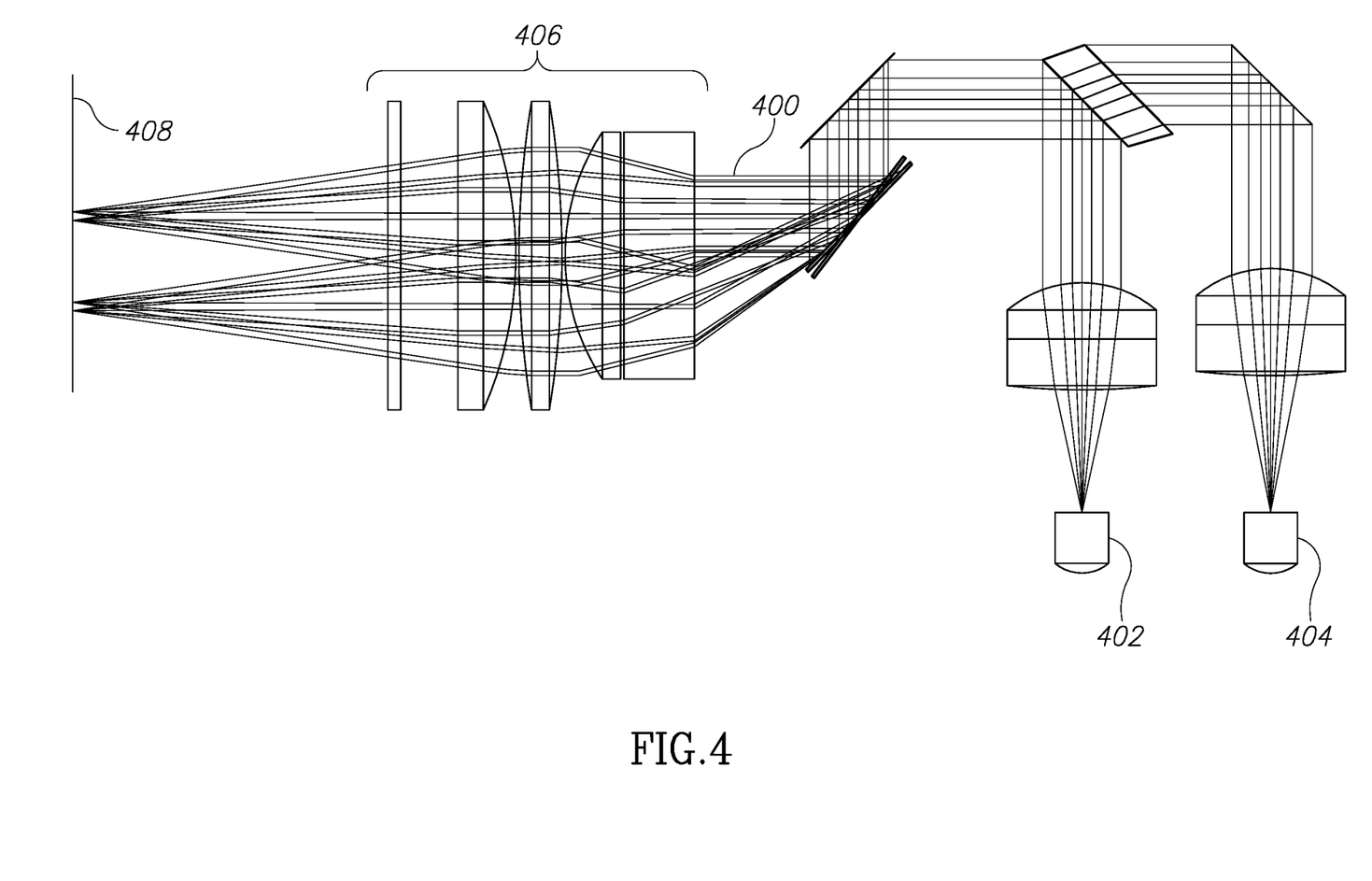
FIG. 4 illustrates the optical light paths of the two wavelength laser beams.

FIGS. 3 and 4 detail the structure of an embodiment of an optical system that may be used with the device of the present invention. The fiber optics delivery system may be collinear with the exit path of the laser energy, or orthogonal as shown in FIGS. 3 and 4 or any angle in between. The laser energy of both wavelengths may be delivered from the laser module to the handpiece using a single fiber optic cable, two separate fiber optic cables, single fiber bundle or two separate fiber bundles. All instrumentalities in the dual optical train may be contained in a single housing or separate housings closely positioned together.

Turning now to FIG. 3, that figure shows an optical system housing 300 which may be housed within the handpiece of FIG. 2A. In FIG. 3, sources of laser energy in both 1410 nm and 1927 nm wavelengths (302 and 304) are shown to be inputted into the housing 300. Laser energy may be activated within the same or a similar timeframe, with the laser energy beams 306 and 308 being directed to two mirrors, one, mirror 310 for the 1410 nm beam and the other 312 for the 1927 nm beam. Mirror 312 receives the 1927 nm laser beam from the laser source located in a console or other cabinet, which is then reflected in a direction through a second mirror 310. The second mirror is of the type, such as a dichroic mirror, which transmits the 1927 nm laser beam to a third mirror 314 which then directs it to a galvo mirror steering system 316.

The 1410 nm laser beam is directed to the mirror 310, which then reflects the laser beam and directs it to the third mirror 314 which directs it to the galvo mirror steering system 316, which includes a motor 328 for rotating a shaft 324. The shaft may be rotated by the motor 328 in a total angular distance of approximately 15 degrees. The light paths of the two laser beams are illustrated in FIG. 3.

While FIG. 3 shows laser energy beams 306 and 308 as coming from an external source such as a console which includes the laser energy generating sources, wherein the laser energy is conveyed from the console to the handpiece, it is also within the scope of the present invention that one or more of the laser sources may be contained within the handpiece itself.

The purpose of the galvomirror steering system will now be discussed. The galvomirror steering system may be similar to the system used in certain CO2 laser devices manufactured and distributed by Lumenis Ltd, the assignee of the present application. One example of such a steering system is contained in U.S. Pat. No. 6,328,733, assigned to the assignee of the present application. The steering system includes a fourth mirror 320 which is rotatable about an axis 322. The axis includes a shaft 324 which is then movable to a variety of angular positions to reflect and transmit the laser beams of the 1410 nm and the 1927 nm variety coming from the third mirror 314 to the fourth mirror. The laser beams are then transmitted, upon reflection from the fourth mirror 320, to a lens system 326, which directs the laser beams to the target skin tissue. As can be seen in FIG. 3, there are two beams reflected, one in the form of dashed lines and the other in the form of dotted lines, for each of the 1410 nm and the 1927 nm wavelengths. Also, it is seen that the light beams impinging on the fourth mirror 320 are separated due to the light paths chosen, this results in a separation of the laser beams when impinging on the skin tissue.

Under the direction of a programmable controller, which may contained within a console or other device, the laser sources for both the 1410 nm in the 1927 nm may be activated simultaneously and at the same time the steering system moves the fourth mirror, resulting in a pattern pair of non-ablative laser spots directed to the skin tissue. This is further explained below in the section of this application entitled Polytherapy Mode.

While the embodiment is described in terms of employing a galvomirror system, it is to be understood that other known devices, such as MEMs device, may be employed to control the movement of the mirror 320.

FIG. 4 is a figure which shows in particular light paths 400 emanating from both the 1410 nm (402) and the 1927 nm (404) laser beams through the mirrors discussed above and through and into the lens system 406 to then to a focus at a target plane 408 which coincides with the target skin tissue.

III. Polytherapy Mode

Figure 1:
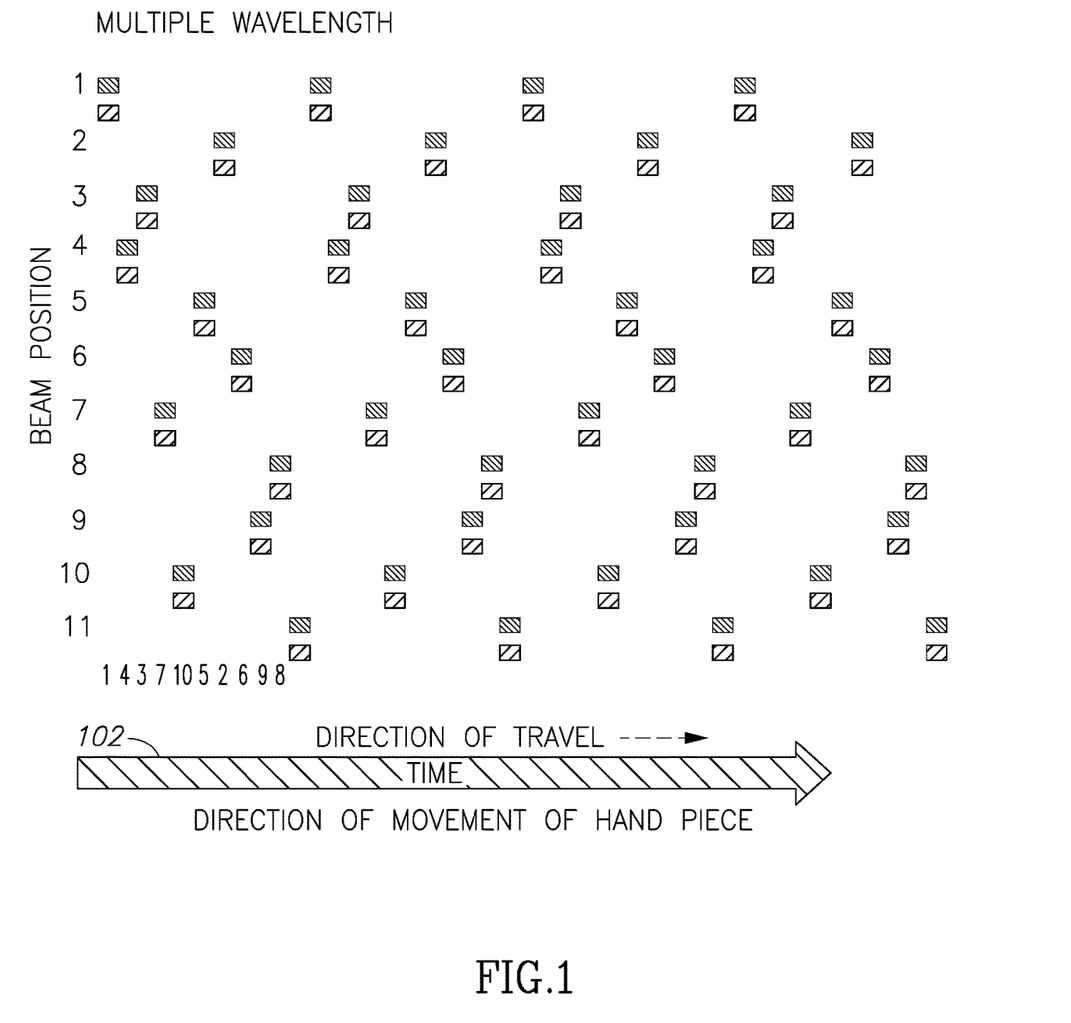
FIGS. 1 and 2 illustrate exemplary laser "spots" deposited on the skin tissue with the device of the present invention.

The present invention may employ what is termed herein "polytherapy" mode, in that one aspect of the invention is the simultaneous application (or nearly so) of two wavelengths of laser light on skin tissue. Examples of how the two lasers may be fired in patterns, such as the patterns shown in FIGS. 1 and 2. In these patterns, one wavelength pattern is shown as solid spots and the other wavelength is shown as hollow spots simply for the purposes of visually distinguishing them on the charts in FIGS. 1 and 2. One of the benefits of such polytreatment is that the treatment can be made more uniform for the two wavelengths and as well patient discomfort is minimized as the lasers "skip around" the areas that are treated. In prior art devices, particularly those that employ two different wavelengths, the firings of the lasers sources are not simultaneous, but rather in seriatim. This may well cause the operator, after the first "pass" with one wavelength, in a second "pass" to hit places on the skin tissue already hit by the laser on the first pass which is generally undesirable as it causes non-uniformity of treatment. Shown in FIGS. 1 and 2 are arrows 102 and 103, denoted as Time, or the passage of time as the treatment handpiece is moved over the skin tissue. Also, the direction of the arrows shows the direction of movement of the handpiece over the skin tissue. While ultimately the choice of the operator, the handpiece maybe moved over the surface of the skin tissue at approximately a velocity of 4-5 cm/sec, but this may be changed to suit the type of treatment and the patient anatomy. Further, since the system is controlled by a galvomirror, while the distance between the spots created by the two laser sources may not be adjustable, the overall distance of the length of the patterns of spots may be adjusted by the galvomirror to suit the type of treatment and the particular portion of the body being treated.

This uniformity of treatment in the present invention is made possible because the deposition of both wavelengths is highly controlled by the controller Such treatment subsequently results in the highly patient desired uniform and even erythema which occurs naturally after such treatments. Another benefit of Polytherapy is the ability to perform a resurfacing and dyspigmentation treatment at the same time, thus significantly minimizing the time of patient discomfort associated with either of these treatments.

As may be seen by comparison of the spot pattern in FIGS. 1 and 2, these are merely two examples of many possible spot patterns which may be determined and input into the controller for spot deposition depending on for example, the part of the body in which the skin tissue is to be treated, the type of treatment, etc.

Turning now first to FIG. 1, this figure is shown as linear, but non-sequential as distributed. This pattern results when positions 1 to 11 are fired in a non-sequential manner (i.e., 1, 4 3, 7, 10, 5 . . . 11). As the handpiece moves in the direction of travel, a pair of con current applications of energy (from different wavelengths in our case) are administered to the skin resulting in the array shown. One set of spots represent one wavelength of treatment light, the other set of spots represent another wavelength. While there are two separate laser sources, both share a single optical train after the third mirror 314. In polytherapy mode, there is a fixed spacing between the two wavelength beams (pairs of beams) perpendicular to the direction of travel. The maximum spacing is dictated by the optical construction of the device (vertical spacing in the view in FIG. 1). Given that the system contains a single axis galvomirror system, the vertical spacing of the overall line of pairs of beams may be adjusted to be smaller than the maximum if so desired.

Turning next to FIG. 2, the pattern shown is both linear and sequential. This pattern results when positions 1-11 are fired in succession (1, 2, 3, etc.) with both wavelengths firing simultaneously in polytherapy mode. The patterns shown in FIGS. 1 and 2 are only exemplary, and different patterns as desired may be implemented.

The desirable spot size on the target skin tissue plane may be about 200μ+/−20%, although the spot size can be adjusted as desired depending on the focal plane of the laser beams onto the target skin tissue. In addition, it may be desirable that the 1410 nm laser be operated at about 5 W, while the 1927 nm laser be operated at about 3 W. However, as with the spot size the power applied to the laser sources may be adjusted according to desirable results.

IV. Rollers, Cooled Rollers and Airflow

Figure 5:
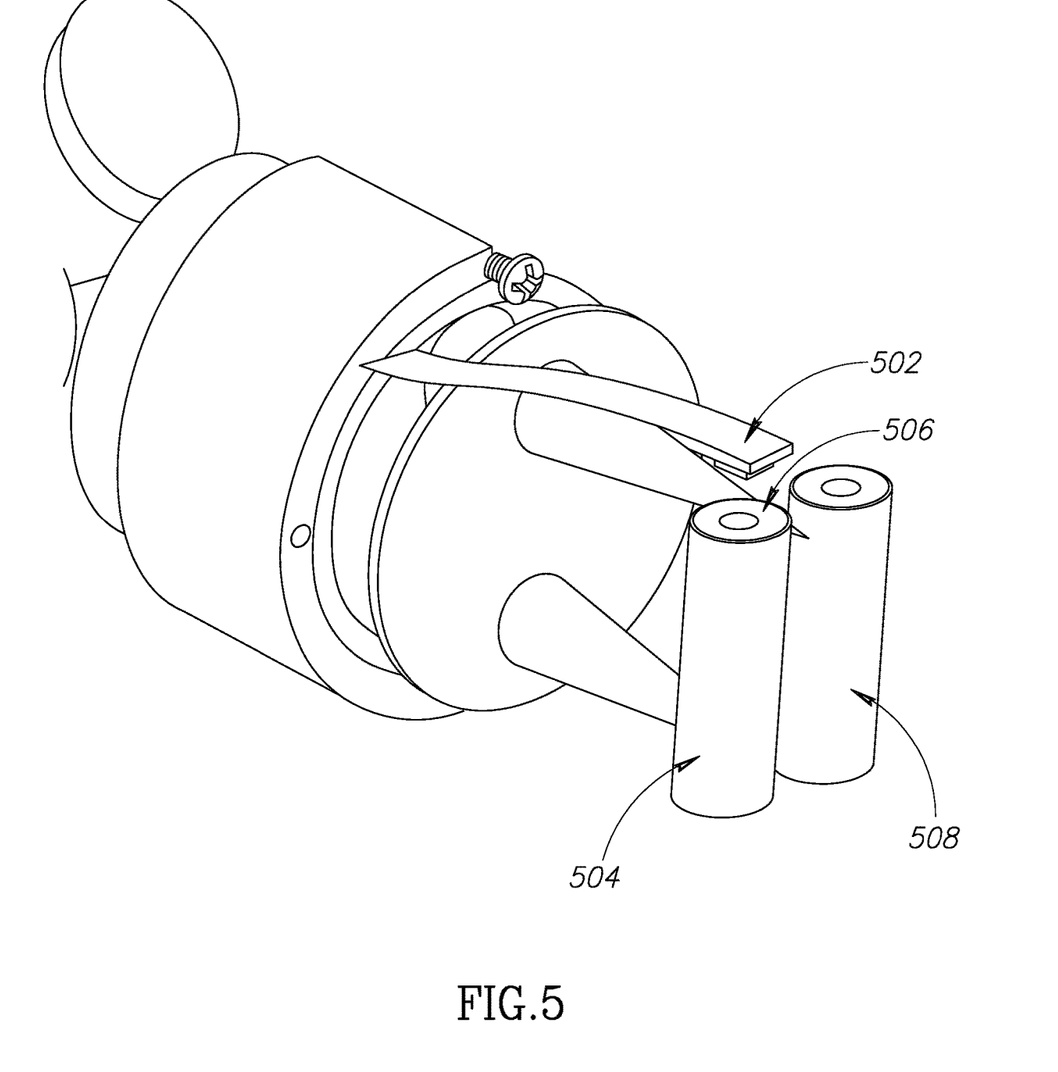
FIG. 5 illustrates the optical system of the present invention together with contact rollers.
Figure 6A:
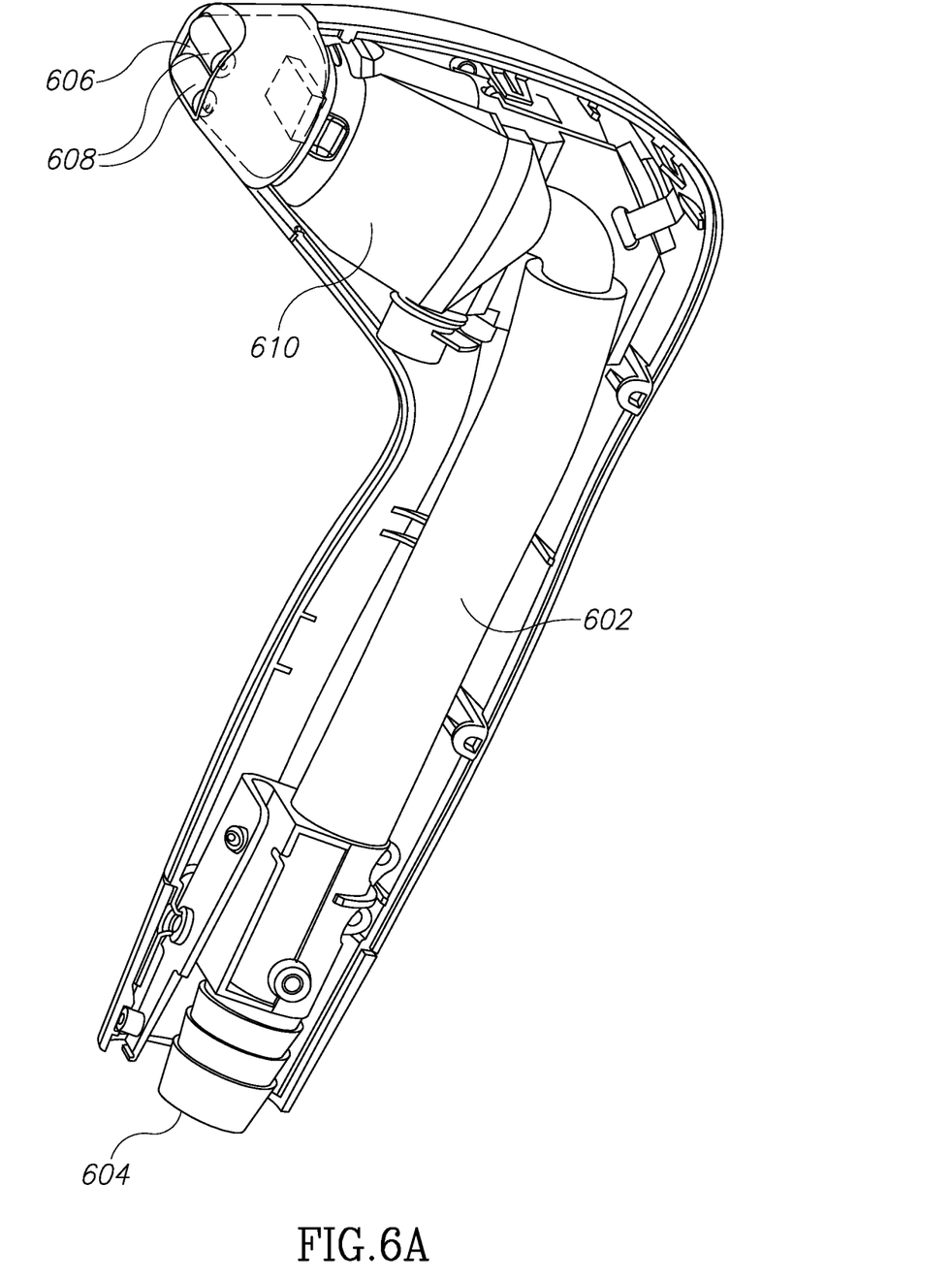
FIGS. 6A and 6B illustrate aspects of the cooling system usable with the handpiece of the present invention.
Figure 6B:
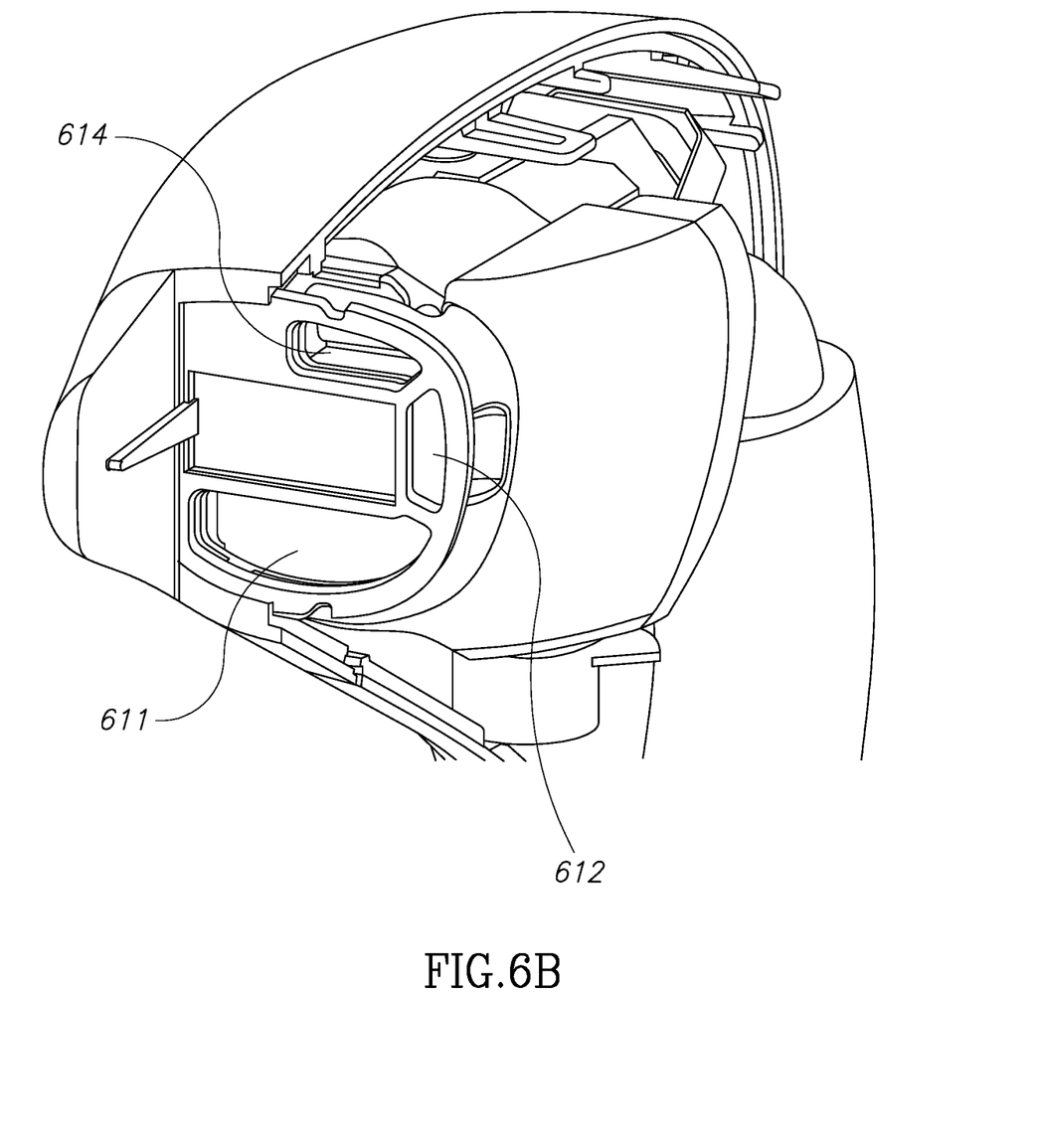

In a number of other skin treatment devices, rollers are known to have been employed, mostly to provide a contact for, by way of example, a RF application or to physically smooth out the skin surface. In the present invention, as illustrated in FIGS. 5, 6A and 6B, rollers may be provided at the distal end 204 of the handpiece to: (1) cool the skin and (2) control firing of the laser beams. On the (1) issue of cooling the targeted skin tissue, one way of accomplishing this is to blow cold air through the handpiece with an air flow channel, as shown in FIGS. 6A and 6B. The cooled air may come from a source within the console of FIG. 2B, operatively associated with the handpiece or from another external source. Also, the rollers may be cooled by the cooled air passing over them or directly through suitable thermoelectric units or even the circulation of a cooled fluid through the rollers. The application of cooled air may be either in a continuous manner or in pulsatile form to take advantage of the so-called "pain gate effect".

It is noted that in the handpieces of FIGS. 6A and 6B, the cooled air flow is applied collinearly with the optical axis. This is believed to be more effective by impinging cooled air directly on the skin tissue, unlike the present convention of a "second pair of hands" holding a cooling nozzle on the side at an angle to the axis of the laser light. Such conventional devices include those made by the Zimmer Company of Germany. Further, integrating the cooling air nozzle with the laser delivery device presents a very ergonomically pleasing design that allows a single operator, for example, to hold the laser delivery device in one hand and stretch the skin with the other hand which is now free of the burden of holding a separate cooling air nozzle.

In addition, the rollers may be useful in metering out the timing of the firings of the laser sources when in contact with the skin. Since the roller or rollers will be placed in contact with the skin tissue and rolled over the surface of the skin, the rotation of the roller or rollers may be utilized in order to time or schedule the firings of the two laser sources.

As illustrated in FIG. 5, a magnetic (or other suitable) sensor 502 may be mounted on or near the distal end of the handpiece and positioned near roller 504, and, as needed, a metal position indicating spot or tracking magnet 506 mounted on or attached to the roller 504 itself. Thus, as the rollers 504 and 508 (508 being a non-tracking roller) are moved along the skin tissue surface, they rotate. The rotation of the magnet inside one of the rollers and corresponding rotation of the magnetic field is sensed by the magnetic sensor which translates this rotation to a linear distance that the handpiece has traveled from one position to the other on the skin tissue surface. The present mechanism allows for dosage or treatment density control in addition to serving as a safety mechanism since the laser will be allowed to fire only if the rollers are in contact with the skin tissue and in motion rolling. Depending on the type of treatment, the sensor causes the two laser beam sources to fire and further the controller causes the galvomirror system to move the mirror 320 shown in FIG. 3 so that a pattern of spots is generated on the target skin tissue.

FIGS. 6A and 6B illustrate embodiments of the cooling system integrated with the handpiece of the present invention. As seen in FIG. 6A, a central channel 602 is formed within the handpiece and conducts cooling air from a suitable source from the proximal 604 to the distal end 606 of the handpiece to impinge first on the rollers 608 and then on the underlying target tissue. Cooling the skin via contact at a lower temperature than the skin, improves patient comfort before during and after treatment. In the type of handpiece shown in FIG. 6A, the cooling airflow from the cooling source is directed from the proximal to the distal end of the handpiece through a combination of tubing 602 and ducting 610.

FIG. 6B illustrates a view of the handpiece tip with the tip and rollers removed to show the three ports 611, 612 and 614 through which cooled air is caused to flow over the rollers (not shown in this figure) and then onto the skin tissue. While three such ports are shown in FIG. 6B, it is to be understood that any number of such ports may be provided to suit the cooling effects desired or required.

What we claim is:

1. A fractional laser treatment device for cosmetically treating skin tissue by providing resurfacing and dyspigmentation treatments simultaneously comprising:
two laser energy generating engines;
each of the two laser generating engines operating to produce non-ablative laser beams at 1410 nm and 1927 nm wavelengths when activated;
a handpiece for receiving the two laser beams generated by the two laser energy generating engines, the handpiece being in operative connection with the at least two laser energy generating engines;
the handpiece including a proximal end and a distal tip, further comprising one or more mirrors along an optical path to receive each of the two laser beams from the proximal end and to convey the two laser beams to the distal tip of the handpiece;
an adjustable beam deflector along the light path between the distal tip and the proximal end of the handpiece;

a controller in the laser treatment device configured to control activation of the two laser energy generating engines and control movement of the adjustable beam deflector;

the controller being configured to: (1) cause activation of both of the two laser energy generating engines at the same time and (2) cause the movement of the adjustable beam deflector such that the two laser beams are deflected to pass through the distal tip of the handpiece and impinge as a pattern of pairs of non-ablative laser spots focused at the skin tissue surface at the same time but separated by a distance and non-overlapping;

further comprising a plurality of rollers mounted distally of the distal tip, the plurality of rollers having an axis of rotation perpendicular with respect to the optical path, such that the handpiece and the plurality of rollers may be configured to be translated along the skin tissue along a direction of travel; and wherein at least one of the plurality of rollers includes an encoding device, and wherein rotation of the plurality of rollers is configured to cause the controller to activate the two laser energy generating engines to lay down the pattern of pairs of non-ablative laser spots along the direction of travel on the skin tissue.

2. The device of claim 1, wherein the adjustable beam deflector is one of: a galvo mirror or a MEMs device.

3. The device of claim 1, wherein the adjustable beam deflector is positioned proximal of the distal tip.

4. The device of claim 3 wherein the one or more mirrors are positioned proximal of the adjustable beam deflector and bend the two laser beams at an angle with respect to the handpiece.

5. The device of claim 1, further comprising one or more lenses distal of the adjustable beam deflector to focus the two laser beams.

6. The device of claim 1, wherein the handpiece further comprises one or more passageways along the light path from the proximal end to the distal tip of the handpiece to carry air from an external source to the distal tip of the handpiece and then the skin tissue.

7. The device of claim 6, wherein the external source provides cooling air to cool the skin tissue and to impinge upon and cool the plurality of rollers.

8. A method for fractionally treating skin tissue cosmetically by providing resurfacing and dyspigmentation treatments simultaneously comprising:

providing two laser energy generating engines, wherein each of the two laser generating engines operate to produce laser beams at 1410 nm and 1927 nm wavelengths;

providing a handpiece for receiving the two laser beams generated by the two laser energy generating engines, the handpiece being in operative connection with the two laser energy generating engines;

wherein the handpiece includes a proximal end and a distal tip, further comprising one or more mirrors along an optical path to receive each of the two laser beams from the proximal end and to convey the two laser beams to the distal tip of the handpiece;

providing an adjustable beam deflector along the light path between the distal tip and the proximal end of the handpiece;

providing a controller in the laser treatment device to control activation of the two laser energy generating engines and control movement of the adjustable beam deflector;

the method further comprising: the controller: (1) causing the activation of both of the two laser energy generating engines at the same time and (2) causing the movement of the adjustable beam deflector such that the two laser beams are deflected to pass through the distal tip of the handpiece and impinge as a pattern of pairs of laser spots focused at the skin tissue surface at the same time but separated by a distance and non-overlapping;

further comprising a plurality of rollers mounted distally of the distal tip, the rollers having an axis of rotation perpendicular with respect to the optical path, such that the handpiece and the plurality of rollers may be translated along the skin tissue along a direction of travel; and wherein at least one of the plurality of rollers includes an encoding device, and wherein rotation of the plurality of rollers causing the controller to activate the two laser energy generating engines to lay down the pattern of pairs of non-ablative laser spots along the direction of travel on the skin tissue.

9. The method of claim 8, wherein the adjustable beam deflector is one of: a galvo mirror or a MEMs device.

10. The method of claim 8, wherein the adjustable beam deflector is positioned proximal of the distal tip.

11. The method of claim 10 wherein the one or more mirrors are positioned proximal of the adjustable beam deflector and bend the two laser beams at an angle with respect to the handpiece.

12. The method of claim 8, further comprising one or more lenses distal of the adjustable beam deflector to focus the two laser beams.

13. The method of claim 8, wherein the handpiece further comprises one or more passageways along the light path from the proximal end to the distal tip of the handpiece to carry air from an external source to the distal tip of the handpiece and then the skin tissue.

14. The method of claim 13, wherein the external source provides cooling air to cool the skin tissue and to impinge upon and cool the plurality of rollers.

* * * * *